United States Patent [19]

Lamothe et al.

[11] Patent Number: 5,518,733
[45] Date of Patent: May 21, 1996

[54] COSMETIC COMPOSITIONS CONTAINING OLIGOSACCHARIDES

[75] Inventors: Jean-Pierre H. G. Lamothe, Toulouse; Yves G. Marchenay, Boulogne; Pierre F. Monsan, Blagnac; François M. B. Paul; Vincent Pelenc, both of Toulouse, all of France

[73] Assignee: Bioeurope, Toulouse, France

[21] Appl. No.: 167,858

[22] PCT Filed: Jun. 26, 1992

[86] PCT No.: PCT/FR92/00597

§ 371 Date: Dec. 23, 1993

§ 102(e) Date: Dec. 23, 1993

[87] PCT Pub. No.: WO93/00067

PCT Pub. Date: Jan. 7, 1993

[30] Foreign Application Priority Data

Jun. 27, 1991 [FR] France .................................. 91 07955

[51] Int. Cl.$^6$ ................................ A61K 6/06; A61K 7/00
[52] U.S. Cl. ....................... 424/430; 424/401; 424/70.13; 514/53; 514/54; 514/61
[58] Field of Search ..................... 424/401, 430, 424/195.1, 70, 70.13; 514/53, 54, 61

[56] References Cited

U.S. PATENT DOCUMENTS

| | | | |
|---|---|---|---|
| 2,726,190 | 12/1955 | Koepsell | 195/31 |
| 3,894,146 | 7/1975 | Tsuyama | 424/49 |
| 4,340,673 | 6/1982 | Stoudt | 435/97 |
| 4,364,837 | 12/1982 | Pader | 252/173 |
| 4,435,389 | 3/1984 | Mutai | 424/181 |
| 4,518,581 | 5/1985 | Miyake | 424/48 |
| 4,812,444 | 3/1989 | Mitsuhashi et al. | 514/53 |
| 4,987,124 | 1/1991 | Speights | 514/23 |
| 5,087,449 | 2/1992 | Masai | 424/195.1 |
| 5,164,183 | 11/1992 | Komoda | 424/195.1 |

FOREIGN PATENT DOCUMENTS

| | | |
|---|---|---|
| 0480640 | 4/1992 | European Pat. Off. |
| 60-190703 | 9/1985 | Japan. |
| 62-000412 | 1/1987 | Japan. |
| 01037255 | 2/1989 | Japan. |
| 03117465 | 5/1991 | Japan. |

*Primary Examiner*—Thurman K. Page
*Assistant Examiner*—Sally Gardner
*Attorney, Agent, or Firm*—Watson Cole Stevens Davis

[57] ABSTRACT

Cosmetic compositions providing a suitable medium for the development of beneficial endogenous flora, and including at least one oligosaccharide selected from the group consisting of gluco-oligosaccharides, fructo-oligosaccharides, α- and β-galacto-oligosaccharides and mixtures thereof. Examples of compositions are liquid soap, body lotion, face cream and vaginal gel.

5 Claims, No Drawings

COSMETIC COMPOSITIONS CONTAINING OLIGOSACCHARIDES

The invention relates to cosmetic compositions containing oligosaccharides.

Man and animals are host to populations of microorganisms which develop naturally both at the surface and in the cavities of their bodies. These microbial flora, or endogenous microflora, are characteristic of the species and of the region of the body where they develop. In close contact with their host, certain microorganisms are known to have a beneficial action on the skin or vaginal mucous membrane, for example by maintaining a slightly acidic environment and/or by participating in the protection of the organism against infections by pathogenic microorganisms which are present in small numbers or which are not usually present on the skin or on the vaginal mucous membrane.

It would therefore be useful to have available cosmetics which create a medium favorable for the development of the beneficial endogenous flora and which orient the metabolism of the whole endogenous microflora such that the said microflora participates in maintaining the good physico-chemical balance of the skin and the mucous membranes while not concomitantly favoring the development of pathogenic microorganisms.

During extensive research studies, the Applicant has found that certain oligosaccharides constitute products which can be easily metabolized by several beneficial strains of the skin microflora and of the vaginal flora. A substantial gluco-oligosaccharide metabolism by non-pathogenic strains such as *Micrococcus kristinae, Micrococcus sedentarius, Staphylococcus capitis, Corynebacterium xerosis* and *Lactobacillus pentosus* has thus been observed during in vitro culture studies. On the other hand, pathogenic or opportunistic strains such as *Staphylococcus aureus, Gardnerella vaginalis* and *Propionibacterium acnes* do not metabolize, or very slightly metabolize these oligosaccharides.

Furthermore, it has also been observed that, in the presence of these oligosaccharides, certain strains such as *Lactobacillus pentosus, Micrococcus kristinae, Gardnerella vaginalis, Propionibacterium avidum* and *Propionibacterium granulosum*, acidify the culture medium. Lactobacilli produce in particular lactic acid.

The invention therefore relates to cosmetic compositions, characterized in that they comprise at least one oligosaccharide chosen from the group consisting of gluco-oligosaccharides, fructo-oligosaccharides, α- and β-galacto-oligosaccharides and mixtures thereof.

Glucosaccharides which can be used in the cosmetic compositions of the invention are especially gluco-oligosaccharides corresponding to the general formula:

$$(O\text{-}\alpha\text{-}D\text{-glucopyranosyl})_n\text{-}A$$

where A is a residue of a glucose-accepting sugar chosen from maltose, isomaltose, isomaltotriose, methyl α-glucoside and glucose, and n=1 to 10, the glucoside bonds being of the α(1→6) and, optionally, α(1→2) and/or α(1→3) type, the α(1→2) bond, if present, being situated at the non-reducing end or constituting a branch point.

The above oligosaccharides can be produced by known processes for enzymatic synthesis by means of the enzyme glucosyl-transferase derived from the bacteria Leuconostoc mesenteroides, in the presence of sucrose and a glucose-accepting sugar chosen from maltose, isomaltose, isomaltotriose, methyl α-glucoside and glucose.

Such processes are described in the literature, for example in EP-A-0,325,872, by Paul et al. in Carbohydrate Research, 149 (1986), pages 433–441 and in U.S. Pat. No. 2,726,190. Strains of Leuconostoc mesenteroides which are preferred for the implementation of the process of synthesis are the strains NRRL B-512(F) (for the production of gluco-oligosaccharides with only α(1→6) bonds) and NRRL B-1299 (for the production of gluco-oligosaccharides with α(1→6) and α(1→2) bonds).

Maltose is most particularly preferred as glucose-accepting sugar.

Useful fructo-oligosaccharides, separately or in the form of a mixture, are especially those corresponding to the general formula GFn or to the general formula Fm where G is a glucose residue, F a fructose residue and n equals 1 to 10, in particular 2 to 4, and m equals 1 to 10, in particular 2 to 4. Such fructo-oligosaccharide exist in the natural state in a number of plants such as onion, garlic, artichoke, chicory and the like. They can be synthesized by the action, on sucrose, of a transfer enzyme, fructosyl transferase, extracted from an Aspergillus. Useful branched fructo-oligosaccharides can also be prepared from inulin from chicory roots by enzymatic processes, as described in WO-A1-91 13076.

Useful fructo-oligosaccharides (also called oligofructoses) are commercially available under the names ACTLIGHT® (sold by Beghin-Meiji Industries, Paris, France) or RATILOSE® (produced by Raffinerie Tirlemontoise, Tienen, Belgium).

Useful α-galacto-oligosaccharides, separately or in the form of a mixture, are especially those which possess a sucrose residue at one of their ends and correspond to the general formula:

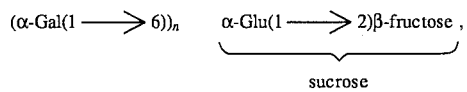

sucrose where n equals 1 to 3, namely raffinose (n=1), stachyose (n=2) and verbascose (n=3) which can be extracted from soyabean. Useful α-galacto-oligosaccharides are available commercially from the Japanese company Calpis Food Industries. See also JP-A2-3 151 854 which describes these compounds. Useful β-galacto-oligosaccharides, separately or in the form of a mixture, are especially those which possess a lactose residue at one of their ends and correspond to the formula:

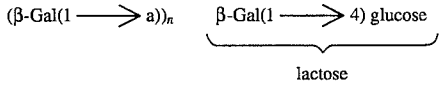

lactose where n=1, 2 or 3 and a=2, 3, 4 and 6, the β(1→6) isomer being predominant. Such β-galacto-oligosaccharides can be obtained by enzymatic synthesis, for example by the action of β-galactosidase in the presence of concentrated lactose, and are available commercially from the Japanese company Yakult Honsha. See also JP-A2-2 156 893 and EP-A-272 095 which describe these compounds and their preparation.

By virtue of the presence of the oligosaccharide, the compositions of the invention make it possible to maintain a medium which is favorable for the development of the beneficial endogenous flora.

The quantity of oligosaccharide present in the cosmetic composition of the invention may range from 0.1% by weight to 20% and more, preferably from 1 to 10% by weight. Below 0.1% by weight, the effect of the oligosaccharide becomes negligible. Furthermore, there is no particular advantage in incorporating more than 20% by weight of oligosaccharide although this is perfectly possible. Considerations of an economic nature also result in limiting the quantity of oligosaccharide to 20% by weight, preferably to 10% by weight, and very advantageously to 5% by weight.

Usually, the oligosaccharide constituent will constitute a mixture of oligosaccharides in so far as the processes for the manufacture of the compounds produce such mixtures.

In addition to the oligosaccharide constituent, the cosmetic compositions of the invention may contain the ingredients usually incorporated into this type of composition. It goes without saying, obviously, that it is advisable to avoid incorporating into the compositions ingredients whose properties would interfere with the desired aim which is to favor the development of the beneficial skin or vaginal microflora and the preservation of acidic conditions.

Thus, it is advisable to avoid incorporating bactericidal ingredients in proportions which would anhilate the endogenous microflora, or ingredients which confer a pronounced basic character on the composition.

For example, it will be good to avoid using high proportions of ionic surface-active agents such as sodium lauryl sulfate, whose bactericidal properties are well known. If there is a need to incorporate a high proportion a surface-active agent into the composition (for example in the case of a liquid soap or a shampoo), a non-ionic surface-active agent such as an alkyl glucoside or a dialkyl ester will be used instead.

Nevertheless, incorporating into the compositions of the invention a small proportion (for example less than 1% by weight) of preserving agent having a bacteriostatic and, optionally an antifungal action can be tolerated in order to allow the preservation of the said compositions for long periods.

Advantageously, the cosmetic compositions of the invention contain an acidic buffer which adjusts the pH of the composition to the 5 to 7 range, preferably 5 to 6, such as a malic acid/sodium malate buffer, so as to favor rapid reimplantation of the microflora.

The oligosaccharides can be incorporated into a wide variety of cosmetic compositions such as liquid soap, shampoo, body milk, face cream, vaginal gel and the like.

These compositions can be easily prepared by techniques commonly used in the cosmetics industry.

In order to illustrate the invention, the following non-restrictive examples of cosmetic compositions according to the invention are given below.

In examples 1 to 5, the oligosaccharide constituent used was a mixture of gluco-oligosaccharides produced by the company BIOEUROPE in accordance with the teachings of EP-A-0,325,872, using maltose as glucose-accepting sugar and glucosyl-transferase derived from the strain Leuconostoc mesenteroides NRLL B-1299. This mixture of glucose-oligosaccharides with $\alpha(1\rightarrow 6)$ and $\alpha(1\rightarrow 2)$ bonds was predominantly made up of oligosaccharides with the degrees of polymerization 3 to 7 (n=1 to 5).

In the examples, all the proportions indicated are in % by weight.

EXAMPLE 1

Liquid Soap

| | |
|---|---|
| Gluco-oligosaccharides "Bioeurope" | 5 |
| Non-ionic surface-active agent (ORAMIX ®NS10) | 18 |
| Thickener (Sepigel ® 305) | 2 |
| Preservative (Sepicide ®HB) | 0.7 |
| Malic acid/sodium malate buffer (qs pH 5.5) # | 0.10 |
| Water | qs 100 |

Notes:
ORAMIX ®NS10 is an alkyl glucoside sold by the company SEPPIC.

SEPIGEL® 305 is a thickening and stabilizing agent for emulsions sold by the company SEPPIC, which is provided in the form of a neutral fluid emulsion. It is a polymeric material referenced under the name: polyacrylamide (and) isoparaffin (and) laureth-7 (CTFA name).

SEPICIDE® HB is a liquid preserving agent, sold by the company SEPPIC, for the protection of health care and beauty products against microbial contamination. It consists of methyl, ethyl, propyl and butyl esters of para-hydroxybenzoic acid in combination with phenoxyethyl alcohol.

EXAMPLE 2

Shampoo

| | |
|---|---|
| Gluco-oligosaccharide "Bioeurope" | 5 |
| Surface-active agent of Ex. 1 | 10 |
| Polysorbate 80 | 5 |
| Preservative of Ex. 1 | 0.7 |
| Buffer of Ex. 1 | (qs pH 5.5) # 0.1 |
| Water | qs 100 |

Note:
Polysorbate 80 is an emulsifier. It is a polyoxyethylene (20)-sorbitan monooleate.

EXAMPLE 3

Body Milk (emulsion)

| | |
|---|---|
| Gluco-oligosaccharide "Bioeurope" | 5 |
| Cetyl and stearyl octanoate (fatty phase) | 10 |
| Polysorbate 80 | 3.6 |
| Glycol palmitate (fatty phase) | 2.0 |
| Thickener of Ex. 1 | 1.5 |
| Sorbitan ester (emulsifying agent) | 0.7 |
| Preservative of Ex. 1 | 0.7 |
| Buffer of Ex. 1 | qs pH6 |
| Water | qs 100 |

EXAMPLE 4

Face Cream (emulsion)

| | |
|---|---|
| Gluco-oligosaccharide "Bioeurope" | 5 |
| Cetyl and stearyl octanoate (fatty phase) | 3 |
| Polysorbate 80 | 5 |
| Micropearl M 100 (pearlescent agent sold by the Japanese company Matsumoto) | 3 |
| Preservative of Ex. 1 | 0.7 |
| Buffer of Ex. 1 | qs pH6 |
| Water | qs 100 |

EXAMPLE 5

Vaginal Gel

| | |
|---|---|
| Gluco-oligosaccharide "Bioeurope" | 5 |

| | |
|---|---|
| Thickener of Ex. 1 | 3 |
| Preservative of Ex. 1 | 0.7 |
| Buffer of Ex. 1 | qs pH6 |
| Water | qs 100 |

EXAMPLE 6

Cosmetic compositions similar to those of Examples 1 to 5 were prepared except that the above described gluco-oligosaccharide "Bioeurope" was replaced by a gluco-oligosaccharide produced in a manner similar to gluco-oligosaccharide "Bioeurope" but using the glucosyl-transferase obtained from the strain Leuconostoc mesenteroides NRLL B-512(F).

The resultant gluco-oligosaccharide had only α(1→6) glucoside bonds.

The cosmetic compositions thus produced had properties comparable to those of Examples 1–5.

EXAMPLE 7

Cosmetic compositions similar to those of Examples 1 to 5 were prepared except that the above-described gluco-oligosaccharide "Bioeurope" was replaced by identical quantities of the fructo-oligosaccharides ACTILIGHT® P available from the company Beghin-Meiji Industries.

The cosmetic compositions thus produced had properties comparable to those of Examples 1–5.

EXAMPLE 8

Cosmetic compositions similar to those of Examples 1 to 5 were prepared except that the above-described gluco-oligosaccharide "Bioeurope" was replaced by 25% higher quantities of the fructo-oligosaccharide RAFTILOSE® L55 syrup (containing 80% dry extract).

EXAMPLE 9

Cosmetic compositions similar to those of Examples 1 to 5 were prepared except that the above-described gluco-oligosaccharide "Bioeurope" was replaced by similar quantities of the α-galacto-oligosaccharides extracted from soyabean available from the company Calpis Food Industry Co., Ltd.

EXAMPLE 10

Cosmetic compositions similar to those of Examples 1 to 5 were prepared except that the above-described gluco-oligosaccharide "Bioeurope" was replaced by similar quantities of the β-galacto-oligosaccharides available from the Japanese company Yakult Honsha.

The cosmetic compositions thus produced had properties comparable to those of Examples 1–5.

It goes without saying that the embodiments described are merely examples and they can be modified, especially by substitution of equivalent techniques, without as a result departing from the framework of the invention.

We claim:

1. A method for favoring the development, on human skin or vagina, of at least one strain selected from the group consisting of *Micrococcus kristinae, Micrococcus sedentarius, Staphylococcus capitis, Corynobacterium xerosis* and *Lactobacillus pentosus*, which comprises the step of:

applying to said human skin or vagina a composition comprising at least 0.1% by weight of at least one oligosaccharide selected from the group consisting of gluco-oligosaccharides of the general formula:

$$(O\text{-}\alpha\text{-}D\text{-glucopyranosyl})_n\text{-}A$$

wherein A is a residue of a glucose-accepting sugar selected from the group consisting of maltose, isomaltose, isomaltotriose, methyl α-glucoside and glucose, and n=1 to 10, the glucoside bonds being α(1→2) and/or α(1→3), the optional α(1→2) bond being situated at a non-reducing end of the oligosaccharide molecule or constituting a branching point of said molecule;

fructo-oligosaccharides of the general formulae GFn or an oligosaccharide of the general formula, Fm wherein G is a glucose residue, F a fructose residue, n=1 to 10 and m=1 to 10;

α-galacto-oligosaccharides of the general formula:

$$(\alpha\text{-}Gal(1\to 6))_n\alpha\text{-}Glu(1\to 2)\beta\text{-fructose},$$

wherein n=1, 2 or 3;

β-galacto-oligosaccharides of the general formula $$(\beta\text{-}Gal(1\to a))_n\beta\text{-}Gal(1\to 4)\text{glucose}$$

wherein n=1, 2 or 3 and a=6 and 2, 3 or 4;

and mixtures thereof;

said composition having a pH of 5 to 7.

2. The method according to claim 1, wherein said composition comprises from 0.1 to 20% by weight of said oligosaccharide.

3. The method according to claim 1, wherein said composition further comprises a non-ionic surface-active agent.

4. The method according to claim 1, wherein said composition further comprises a buffer which maintains the pH at 5 to 7.

5. The method according to claim 1, wherein said composition is applied in the form of a liquid soap, a shampoo, a body milk, a face cream or a vaginal gel.

* * * * *